United States Patent [19]

Van Duzee

[11] 4,246,285
[45] Jan. 20, 1981

[54] SKIN CONDITIONING COMPOSITIONS CONTAINING GUANIDINE INORGANIC SALTS

[75] Inventor: Barry F. Van Duzee, Cincinnati, Ohio

[73] Assignee: The Procter & Gamble Company, Cincinnati, Ohio

[21] Appl. No.: 624,202

[22] Filed: Oct. 20, 1975

[51] Int. Cl.³ .................... A61K 7/025; A61K 7/48
[52] U.S. Cl. ........................................ 424/358; 424/47; 424/64; 424/168; 424/326; 424/362; 424/366
[58] Field of Search ............... 424/326, 358, 366, 168, 424/47

[56] References Cited

U.S. PATENT DOCUMENTS

| | | | |
|---|---|---|---|
| 2,620,301 | 12/1952 | Mc Leod | 252/33.4 X |
| 3,152,181 | 10/1964 | Shapiro | 424/115 X |
| 3,479,437 | 11/1969 | Szabo et al. | 424/319 X |
| 3,628,941 | 12/1971 | Marks | 424/358 X |
| 3,769,427 | 10/1973 | Hughes | 424/358 X |
| 3,843,798 | 10/1974 | Cook et al. | 424/319 |

FOREIGN PATENT DOCUMENTS 1218107  12/1959  France ...................................... 424/326

OTHER PUBLICATIONS

Martindale The Extra Pharmacopoeia, 24th Ed., vol. I, 1958, p. 1372.
Chem. Abs., 1953, vol. 47, p. 2973.

Primary Examiner—Dale R. Ore
Attorney, Agent, or Firm—Richard C. Witte; Jerry J. Yetter; Michael J. Roth

[57] ABSTRACT

A skin conditioning composition containing a guanidine inorganic salt. The compositions are in the form of lotions, creams, solutions, gels, and solids.

16 Claims, No Drawings

SKIN CONDITIONING COMPOSITIONS CONTAINING GUANIDINE INORGANIC SALTS

BACKGROUND OF THE INVENTION

The present invention relates to skin conditioning compositions. More particularly the invention relates to the use of guanidine inorganic salts in skin conditioning compositions.

Compositions which improve the condition of skin through moisturization and flexibilization are provided herein. The treatment of human skin with various agents has been undertaken for many years with the goal being to keep the skin in a smooth and supple condition. Skin has the tendency to dry out when exposed to conditions of low humidity and/or low temperature. Under normal conditions the water content and vapor pressure of the epidermis are higher than those of the surrounding air with a consequent evaporation of water from the skin surface. Skin becomes dry because of the excess loss of water from the surface and the subsequent loss of water from the stratum corneum.

Application of oils or oil and water emulsions to the skin so as to form a barrier which reduces the escape of moisture from the skin is known to the art. Increased moisture content is believed to be either directly or indirectly responsible for increasing the flexibility of the skin. Many different emollients have been suggested as useful for application to the skin to impart a benefit thereto. See for example *Cosmetics Science & Technology*, 2nd ed., Vol. 1, pages 34–36. Urea is another compound which has been suggested for use in skin conditioning compositions. See U.S. Pat. No. 3,666,863, May 30, 1972, Swanbeck.

There is a continuing need for additional skin conditioning agents. Such agents must not only be able to impart a desirable benefit to the skin, but must be economical and be capable of being formulated in a wide variety of formulations.

It is an object of this invention to provide a skin conditioning composition which is capable of delivering a desirable benefit to the skin.

It is another object of this invention to provide skin conditioning compositions containing guanidine inorganic salts as a skin conditioning component.

These and other objects will become apparent from the description to follow.

As used herein all percentages and ratios are by weight unless otherwise indicated.

SUMMARY OF THE INVENTION

There is provided skin conditioning compositions containing guanidine inorganic salts. The compositions are in the form of lotions, creams, solutions, gels and solids.

DESCRIPTION OF THE INVENTION

The compositions of this invention consist essentially of guanidine inorganic salts and a cosmetically acceptable vehicle capable of delivering the guanidine to the skin. The compositions of this invention contain from 1% to 30%, preferably 2% to 15%, most preferably 5% to 10%, of the guanidine inorganic salt with the balance being the cosmetically acceptable vehicle.

Inorganic salts of guanidine are well known compounds and are commercially available. Any inorganic salt of guanidine is used in the present invention. Examples of suitable guanidine inorganic salts are: guanidine carbonate, guanidine hydrochloride, guanidine bisulfite, guanidine sulfate, guanidine phosphate and guanidine hydrobromide. The guanidine inorganic salt is used at a level from 1% to 30% in the compositions of this invention. A level below 1% does not provide a noticeable skin conditioning benefit while levels above 30% do not provide additional skin conditioning benefits and are avoided for this reason.

The cosmetically acceptable vehicle is any suitable vehicle capable of delivering the guanidine inorganic salt to the skin. A wide variety of cosmetically acceptable vehicles are known and are used herein. Generally, the cosmetically acceptable vehicles are organic in nature and are capable of having dispersed or dissolved therein the guanidine inorganic salts. *Cosmetics Science and Technology*, 2nd ed., Vol. 1, contains numerous examples of suitable cosmetically acceptable vehicles.

The physical form of the skin conditioning compositions is not critical. The compositions are in a lotion, cream, solution, gel or solid form. Description of the forms and preferred skin conditioning compositions follow.

Skin Conditioning Lotions

Skin conditioning lotions contain from 1% to 30%, preferably 2% to 10% of the guanidine inorganic salt, from 1% to 25%, preferably 3% to 15% of an emollient, and the balance water. Several emollients are known. Examples of classes of emollients and examples thereof follow.

1. Hydrocarbon oils and waxes. Examples thereof are mineral oil, petrolatum, parrafin, ceresin, ozokerite, microcrystalline wax, polyethylene, and perhydrosqualene.

2. Silicone oils, such as dimethyl polysiloxanes, methylphenyl polysiloxanes, water-soluble and alcohol-soluble silicone glycol copolymers.

3. Triglyceride esters, for example vegetable and animal fats and oils. Examples include caster oil, safflower oil, cottonseed oil, corn oil, olive oil, cod liver oil, almond oil, avocado oil, palm oil, sesame oil, and soybean oil.

4. Acetoglyceride esters, such as acetylated monoglycerides.

5. Ethoxylated glycerides, such as ethoxylated glyceryl monostearate.

6. Alkyl esters of fatty acids having 10 to 20 carbon atoms. Methyl, isopropyl, and butyl esters of fatty acids are useful herein. Examples include hexyl laurate, isohexyl laurate, isohexyl palmitate, isopropyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristyl lactate, and cetyl lactate.

7. Alkenyl esters of fatty acids having 10 to 20 carbon atoms. Examples thereof include oleyl myristate, oleyl stearate, and oleyl oleate.

8. Fatty acids having 10 to 20 carbon atoms. Suitable examples include pelargonic, lauric, myristic, palmitic, stearic, isostearic, hydroxystearic, oleic, linoleic, ricinoleic, arachidic, behenic, and erucic acids.

9. Fatty alcohols having 10 to 20 carbon atoms. Lauryl, myristyl, cetyl, hexadecyl, stearyl, isostearyl, hydroxystearyl, oleyl, ricinoleyl, behenyl, erucyl, and 2-octyl dodecanol alcohols are examples of satisfactory fatty alcohols.

10. Fatty alcohol ethers. Ethoxylated fatty alcohols of 10 to 20 carbon atoms include the lauryl, cetyl, stearyl, isostearyl, oleyl, and cholesterol alcohols having attached thereto from 1 to 50 ethylene oxide groups or 1 to 50 propylene oxide groups.

11. Ether-esters such as fatty acid esters of ethoxylated fatty alcohols.

12. Lanolin and derivatives. Lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin, acetylated lanolin alcohols, lanolin alcohols linoleate, lanolin alcohols ricinoleate, acetate of lanolin alcohols ricinoleate, acetate of ethoxylated alcohols-esters, hydrogenolysis of lanolin, ethoxylated hydrogenated lanolin, ethoxylated sorbitol lanolin, and liquid and semisolid lanolin absorption bases are illustrative of emollients derived from lanolin.

13. Polyhydric alcohols and polyether derivatives. Propylene glycol, dipropylene glycol, polypropylene glycol 2000, 4000, polyoxyethylene polyoxypropylene glycols, polyoxypropylene polyoxyethylene glycols, glycerol, ethoxylated glycerol, propoxylated glycerol, sorbitol, ethoxylated sorbitol, hydroxypropyl sorbitol, polyethylene glycol 200–6000, methoxy polyethylene glycols 350, 550, 750, 2000, 5000, poly[ethylene oxide] homopolymers (100,000–5,000,000), polyalkylene glycols and derivatives, hexylene glycol (2-methyl-2,4-pentanediol), 1,3-butylene glycol, 1,2,6-hexanetriol, ethohexadiol USP (2-ethyl-1,3-hexanediol), $C_{15}$–$C_{18}$ vicinal glycol, and polyoxypropylene derivatives of trimethylolpropane are examples thereof.

14. Polyhydric alcohol esters. Ethylene glycol mono- and di-fatty acid esters, diethylene glycol mono- and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

15. Wax esters such as beeswax, spermaceti, myristyl myristate, stearyl stearate.

16. Beeswax derivatives, e.g. polyoxyethylene sorbitol beeswax. These are reaction products of beeswax with ethoxylated sorbitol of varying ethylene oxide content, forming a mixture of ether-esters.

17. Vegetable waxes including carnauba and candelilla waxes.

18. Phospholipids such as lecithin and derivatives.

19. Sterols. Cholesterol, cholesterol fatty acid esters are examples thereof.

20. Amides such as fatty acid amides, ethoxylated fatty acid amides, solid fatty acid alkanolamides.

The lotions of this invention can also contain from 1% to 10%, preferably 2% to 5% of an emulsifier. Emulsifiers are of a nonionic, anionic or cationic class. Examples of satisfactory nonionic emulsifiers include fatty alcohols having 10 to 20 carbon atoms, fatty alcohols having 10 to 20 carbon atoms condensed with 2 to 20 moles of ethylene oxide or propylene oxide, alkyl phenols with 6 to 12 carbon atoms in the alkyl chain condensed with 2 to 20 moles of ethylene oxide, mono- and di-fatty acid esters of ethylene glycol wherein the fatty acid moiety contains from 10 to 20 carbon atoms, fatty acid monoglyceride wherein the fatty acid moiety contains from 10 to 20 carbon atoms, diethylene glycol, polyethylene glycols of molecular weight 200 to 6000, propylene glycol of molecular weight 200 to 3000, glycerol, sorbitol, sorbitan, polyoxyethylene sorbitol, polyoxyethylene sorbitan, and hydrophilic wax esters. Suitable anionic emulsifiers include the fatty acid soaps, e.g. sodium, potassium and triethanolamine soaps, wherein the fatty acid moiety contains from 10 to 20 carbon atoms. Other suitable anionic emulsifiers include the alkali metal, ammonium or substituted ammonium alkyl sulfates, alkyl arylsulfonates, and alkyl ethoxy ether sulfonates having 10 to 30 carbon atoms in the alkyl moiety. The alkyl ethoxy ether sulfonates contain from 1 to 50 ethylene oxide units. Satisfactory cationic emulsifiers are the quaternary ammonium, morpholinium and pyridinium compounds. Certain of the emollients described in preceeding paragraphs also have emulsifying properties. When a lotion is formulated containing such an emollient, an additional emulsifier is not needed, though it can be included in the composition.

The balance of the composition comprises water. The lotions may be formulated by simply admixing all of the components together. Preferably the guanidine inorganic salt is dissolved in the water and the mixture is added to the emollient. Optional components such as the emulsifier or common additives are included therein. One common additive is a thickening agent at a level from 1% to 10% of the composition. Examples of suitable thickening agents include: cross-linked carboxy polymethylene polymers, methyl cellulose, polyethylene glycols, gum tragacanth, gum kharaya, and bentonite.

Skin Conditioning Creams

Skin conditioning compositions of this invention also are formulated in a cream form. The creams consist essentially of from 1% to 30%, preferably 2% to 10% of the guanidine inorganic salt, from 5% to 50%, preferably 10% to 25% of an emollient, and the balance water. The emollients above described are also used in the cream form of the composition. Optionally the cream form contains a suitable emulsifier. Emulsifiers described above are useful herein. When an emulsifier is included, it is in the composition at a level from 3% to 50%, preferably 5% to 20%.

Skin Conditioning Solutions

The compositions of this invention are also formulated in a solution form. The solution form of the composition contains from 1% to 30%, preferably 2% to 15% of the guanidine inorganic salt and the balance a suitable organic solvent. Examples of suitable organic solvents are as follows: propylene glycol, polyethylene glycol (200–600) polypropylene glycol (425–2025), glycerine, sorbitol esters, 1,2,6-hexanetriol, ethanol, isopropanol, butanediol, and mixtures thereof. Such solvent systems may also contain water.

These skin conditioning compositions are applied to the skin in the solution form, or the solutions are formulated in an aerosol form and applied to the skin as a spray-on. The skin conditioning compositions in the aerosol form additionally contain from 25% to 80%, preferably 30% to 50% of a suitable propellant. Examples of such propellants are: the chlorinated, fluorinated and chloro-fluorinated lower molecular weight hydrocarbons. Nitrogen and carbon dioxide are also used as propellant gases. They are used at a level sufficient to expel the contents of the container.

Skin Conditioning Gels

Solution skin conditioning compositions are formulated into a gel form by simply admixing a suitable thickening agent to the above-described solution compositions. Examples of suitable thickening agents are described above with respect to the skin conditioning lotions.

The gelled compositions contain from 1% to 30%, preferably 2% to 15% of the guanidine inorganic salt; from 5% to 75%, preferably 10% to 50% of an organic solvent as above described; from 0.5% to 20%, preferably 1% to 10% of the thickener; and the balance water.

Solid Skin Conditioning Compositions

The compositions of this invention are also formulated into a solid form. Such forms have use as a stick-type composition intended for application to the lips or other parts of the body. Such compositions contain from 1% to 30%, preferably 2% to 15% of the guanidine inorganic salt and from 50% to 99%, preferably 60% to 90% of the above described emollient. This composition can also contain from 1% to 20%, preferably 5% to 15% of a suitable thickening agent, and optionally emulsifiers and water. Thickening agents as described above with respect to the gelled skin conditioning compositions are suitable herein.

Optional Components

The skin conditioning compositions herein can contain conventional cosmetic adjuvants, such as dyes, opacifiers, e.g. titanium dioxide, pigments, perfumes and preservatives. Examples of suitable preservatives are the $C_1$ to $C_4$ alkyl esters of parahydroxy benzoic acid, e.g. methylparahydroxy benzoate, and propylparahydroxy benzoate.

The following examples are illustrative of the invention.

EXAMPLE I

The following skin conditioning solution is tested for its effect upon skin:

| | |
|---|---|
| Propylene glycol | 14% |
| Polyethylene glycol (M.W. = 400) | 6% |
| Guanidine hydrochloride | 5% |
| Water | balance |

Human stratum corneum samples are soaked for 16 hours in the above solution with subsequent drying and rehydration at 88% R.H. Test samples attain equilibrium moisture levels 29% higher than similar samples soaked in identical solutions (excluding the guanidine hydrochloride) under the same conditions. The test samples attain equilibrium moisture levels 47% higher than similar samples soaked in water and tested under the same conditions.

The following examples further illustrate the invention.

EXAMPLE II

| Skin Conditioning Lotion | |
|---|---|
| Mineral oil | 8% |
| Olive oil | 4% |
| Glycerine | 3% |
| Triethanolamine stearate | 5% |
| Guanidine sulfate | 10% |
| Water | Balance |

EXAMPLE III

| Skin Conditioning Cream | |
|---|---|
| Mineral oil | 3% |
| Sorbitol | 15% |
| Triethanolamine stearate | 17% |
| Guanidine phosphate | 6% |
| Water | Balance |

EXAMPLE IV

| Skin Conditioning Gel | |
|---|---|
| Propylene glycol | 14% |
| Polyethylene glycol (M.W. = 400) | 6% |
| Guanidine hydrochloride | 5% |
| Methyl cellulose | 3% |
| Water | Balance |

EXAMPLE V

| Lip Balm | |
|---|---|
| Paraffin | 43% |
| Petrolatum | 25% |
| Mineral oil | 21% |
| Lanolin | 6% |
| Camphor | 17% |
| Menthol | 0.3% |
| Guanidine carbonate | 3% |

What is claimed is:

1. A topical skin care composition in the form of a lotion consisting essentially of:
   (a) from 2% to 15% of a guanidine inorganic salt;
   (b) from 1% to 25% of an emollient; and
   (c) the balance water.

2. The composition of claim 1 wherein the emollient is selected from the group consisting of hydrocarbon oils and waxes, silicone oils, triglyceride esters, acetoglyceride esters, ethoxylated glycerides, alkyl esters of fatty acids, alkenyl esters of fatty acids, fatty acids, fatty alcohols, fatty alcohol ethers, etheresters, lanolin and its derivatives, polyhydric alcohols and polyether derivatives, polyhydric alcohol esters, wax esters, beeswax derivatives, vegetable waxes, phospholipids, sterols, amides, and mixtures thereof.

3. The composition of claim 1 additionally containing from 1% to 10% of an emulsifier.

4. The composition of claim 3 wherein the emulsifier is an organic nonionic surfactant.

5. The composition of claim 1 additionally containing from 1% to 10% of a thickening agent.

6. The composition of claim 2 wherein the guanidine inorganic salt represents 2% to 10% of the composition.

7. The composition of claim 6 wherein the guanidine inorganic salt is selected from the group consisting of guanidine carbonate, guanidine hydrochloride, guanidine bisulfite, guanidine sulfate, guanidine phosphate, guanidine hydrobromide, and mixtures thereof.

8. A topical skin care composition in the form of a cream consisting essentially of:
   (a) from 2% to 15% of a guanidine inorganic salt;
   (b) from 5% to 50% of an emollient; and
   (c) the balance water.

9. The composition of claim 8 wherein the emollient is selected from the group consisting of hydrocarbon oils and waxes, silicone oils, triglyceride esters, acetoglyceride esters, ethoxylated glycerides, alkyl esters of fatty acids, alkenyl esters of fatty acids, fatty acids, fatty alcohols, fatty alcohol ethers, etheresters, lanolin and its derivatives, polyhydric alcohols and polyether derivatives, polyhydric alcohol esters, wax esters, beeswax derivatives, vegetable waxes, phospholipids, sterols, amides and mixtures thereof.

10. The composition of claim 9 wherein the guanidine inorganic salt is present in the composition at a level from 2% to 10% and is selected from the group consisting of guanidine carbonate, guanidine hydrochloride, guanidine bisulfite, guanidine sulfate, guanidine phosphate, guanidine hydrobromide, and mixtures thereof.

11. The composition of claim 8 additionally containing from 3% to 50% of an emulsifier.

12. A topical skin care composition in the form of a solution consisting essentially of:
   (a) from 2% to 15% of a guanidine inorganic salt; and
   (b) the balance a cosmetically acceptable organic solvent selected from the group consisting of propylene glycol, polyethylene glycol, polypropylene glycol, glycerine, sorbitol esters, 1,2,6-hexanetriol, ethanol, isopropanol, butanediol, and mixtures thereof.

13. The composition of claim 12 wherein the guanidine inorganic salt is present at a level from 2% to 15% and is selected from the group consisting of guanidine carbonate, guanidine hydrochloride, guanidine bisulfite, guanidine sulfate, guanidine phosphate, guanidine hydrobromide, and mixtures thereof.

14. The composition of claim 12 additionally containing a propellant material.

15. The composition of claim 12 additionally containing a thickening agent in an amount sufficient to form a gel.

16. The composition of claim 15 wherein the thickening agent represents from 0.5% to 20% and the solvent represents from 5% to 75% of the composition.

* * * * *